US005643272A

United States Patent [19]
Haines et al.

[11] Patent Number: 5,643,272
[45] Date of Patent: Jul. 1, 1997

[54] METHOD AND APPARATUS FOR TIBIAL RESECTION

[75] Inventors: Timothy G. Haines, Stewartsville; David B. Goldstein, Weehawken, both of N.J.

[73] Assignee: Hudson Surgical Design, Inc., Rutherford, N.J.

[21] Appl. No.: 479,363

[22] Filed: Jun. 7, 1995

Related U.S. Application Data

[63] Continuation-in-part of Ser. No. 300,379, Sep. 2, 1994, Pat. No. 5,514,139, and Ser. No. 342,143, Nov. 18, 1994, Pat. No. 5,597,379, which is a continuation-in-part of Ser. No. 300,379.

[51] Int. Cl.[6] .................................................. A61B 17/56
[52] U.S. Cl. ........................................... 606/80; 606/88
[58] Field of Search ................................. 606/88, 87, 86, 606/80, 82, 96

[56] References Cited

U.S. PATENT DOCUMENTS

| | | |
|---|---|---|
| 4,457,307 | 7/1984 | Stillwell . |
| 4,487,203 | 12/1984 | Androphy . |
| 4,566,448 | 1/1986 | Rohr, Jr. . |
| 4,653,488 | 3/1987 | Kenng . |
| 4,722,330 | 2/1988 | Russell et al. . |
| 4,736,737 | 4/1988 | Fargie et al. . |
| 4,787,383 | 11/1988 | Kenna . |
| 4,938,762 | 7/1990 | Wehrli .................................... 606/88 |
| 4,952,213 | 8/1990 | Bowman et al. ........................ 606/79 |
| 5,002,545 | 3/1991 | Whiteside et al. ..................... 606/80 |
| 5,147,365 | 9/1992 | Whitlock et al. ...................... 606/88 |
| 5,228,459 | 7/1993 | Caspari et al. . |
| 5,250,050 | 10/1993 | Poggie et al. .......................... 606/79 |
| 5,263,498 | 11/1993 | Caspari et al. . |
| 5,269,786 | 12/1993 | Morgan ................................... 606/96 |
| 5,284,482 | 2/1994 | Mikhail ................................... 606/86 |
| 5,304,181 | 4/1994 | Caspari et al. ......................... 606/80 |
| 5,306,276 | 4/1994 | Johnson et al. ........................ 606/86 |
| 5,342,368 | 8/1994 | Peterson ................................. 606/88 |

Primary Examiner—Guy V. Tucker
Attorney, Agent, or Firm—Friscia & Nussbaum

[57] ABSTRACT

A method an apparatus for resecting a proximal tibia during a knee replacement operation is provided. The apparatus includes an ankle clamp, an alignment rod, a fixation head, cutting guide clamps having cutting guide slots therein, and a milling bit. The method includes the steps of attaching the ankle clamp about the ankle, interconnecting the distal end of the alignment rod with the ankle clamp, interconnecting the fixation head with the proximal end of the alignment rod, partially attaching the fixation head to the proximal tibia, aligning the alignment rod, completely attaching the fixation head to the proximal tibia, interconnecting the cutting guide clamps with the alignment rod, positioning the cutting guide clamps about the proximal tibia, securing the cutting guide clamps to the tibia at a proper location, removing the fixation head, placing the milling bit within the cutting guide slots, and cutting the proximal tibia with the milling bit.

19 Claims, 8 Drawing Sheets

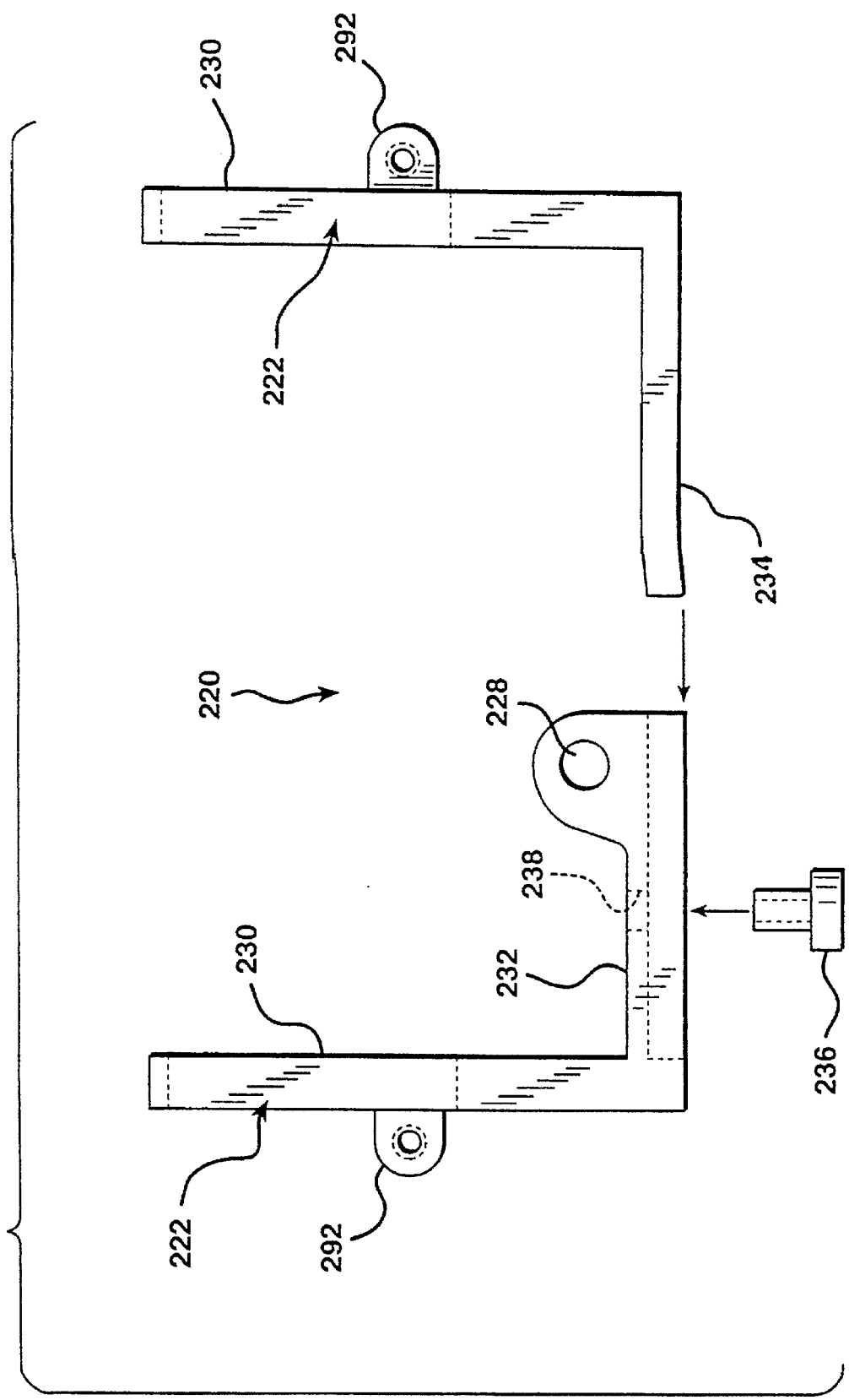

METHOD AND APPARATUS FOR TIBIAL RESECTION

RELATED APPLICATIONS

This application is a continuation-in-part application of U.S. patent application Ser. No. 08/300,379, filed Sep. 2, 1994 by Goldstein, et al., now U.S. Pat. No. 5,514,139. This application is also a continuation-in-part application of U.S. patent application Ser. No. 08/342,143, filed Nov. 18, 1994, by Haines, et al., now U.S. Pat. No. 5,597,379, which is also a continuation-in-part application of U.S. patent application Ser. No. 08/300,379, filed Sep. 2, 1994, by Goldstein, et al., now U.S. Pat. No. 5,514,139. The entire disclosure of these related applications is incorporated herein by reference.

BACKGROUND OF THE INVENTION

1. Field of the Invention

This invention generally relates to a method and apparatus for resecting a proximal human tibia to allow it to properly accept a proximal tibial prosthesis in the context of a total knee replacement operation.

2. Related Art

In the past, efforts have been made to develop methods and apparatus to resect the proximal human tibia in the context of knee replacement surgery. Many of these previous efforts, as shown in the previous relevant patents, align the tibia resection off of the intermedullary canal of the tibia, while others base alignment off of exterior alignment rods. These previous efforts also include alignment adjustment mechanisms, though these mechanisms tend to be complicated and generally inaccurate. None of the methods or apparatus that have been developed can consistently and accurately locate and properly align the tibia resection, while minimizing the cutting skill necessary to properly and safely resect the tibia, as well as smoothly cutting the tibia. Nor do any of the previous efforts disclose a simple but effective method and apparatus for efficiently resecting the proximal tibia. These past efforts include:

Stillwell, U.S. Pat. No. 4,457,307, which discloses a movable saw and saw carriage which may be mounted to the femur for resecting the femur. The saw and saw carriage are adjustable through a plurality of positions to make desired cuts in the femur. Additionally, the device may be used to cut the proximal tibia. First, the knee is extended, the collateral ligaments are tensioned and balanced, and the proximal tibia cortex is scored. Then, the knee is flexed, the saw and saw carriage readjusted, and the tibia cortex cut is completed.

Androphy, U.S. Pat. No. 4,487,203, discloses a knee resection system comprising a guide member, femur and tibia guide rods, a tibia adaptor, a tibia bar, and a femur bar. After the distal femoral condyles are resected, the guide member is attached to the tibia guide rod extending into the tibia. The tibia guide rod has a second guide at a right angle for receiving the guide member. When properly aligned, the guide member is fixed to the anterior side of the proximal tibia with pins. The tibia is then resected with an oscillating saw inserted through slots in the guide member.

Rohr, Jr., U.S. Pat. No. 4,566,488, discloses a ligament tensor device having a first member to engage the tibia and a second member to engage the intercondylar notch of the femur. This device includes means for moving the first member with respect to the second member for applying a selected tension to the ligaments of the knee joint. The device includes a tibia cutting guide which supports a tibia cutting guide head which is positioned and angled to guide the cutting of the tibial plateau. The cutting guide head includes a transverse cutting guide slot. An ankle guide bracket is attached to the lower end of the tibia cutting guide and attaches to the tibia at the ankle for supporting and aligning the tibia cutting guide structure.

Kenna, U.S. Pat. Nos. 4,653,488 and 4,787,383, disclose a tibial cutting jig for cutting a tibia after the femur has been resected. The tibia is aligned off of the resected femur through longitudinal traction and manipulation to bring the ankle under the femur to produce a tibial angle of 2.5 degrees resulting in an overall valgus alignment. The alignment is verified by sight. The knee joint is then immobilized, the transverse tibial cutting jig is pinned to the tibia, the knee is moved to flexion, and the tibia is cut by resting the saw blade on the top surface of the cutting jig.

Russell, et al., U.S. Pat. No. 4,722,330, discloses a distal femoral surface guide for mounting on an intermedullary alignment guide for use in shaping the distal femoral surface. A conventional shaping means such as an oscillating saw or hand saw is introduced into slots in the surface guide to resect the femur. The device also includes stabilizing members that extend along the sides of the femur to stabilize the device.

Fargie, et al., U.S. Pat. No. 4,736,737 discloses a tibial cutting jig having a base that interconnects with an intermedullary alignment rod installed along the axis of the tibia. The base includes outriggers carrying measurement keys for spacing the base a preselected distance above the tibia. A saw guide having slots is attached to the base and is positioned to allow for the cutting of the tibia, by means of an oscillating saw, at a selected position.

Whiteside, et al., U.S. Pat. No. 5,002,545, discloses a shaping device for shaping the tibial plateau comprising an alignment rod located anterior to the anterior cruciate ligament and along the anterior cortex of the intermedullary canal of the tibia. The shaping guide is interconnected with the rod and is adjustable with respect to the rod to control the amount of resection of the tibial plateau by raising or lowering the cutting guide surfaces. The device includes a pin which is inserted into a hole on the alignment guide for setting rotation alignment by aligning the pin with the intercondylar notch of the femur.

Poggie, et al., U.S. Pat. No. 5,250,050 discloses an apparatus for use in preparing the bone surfaces for a total knee prothesis, comprising cutting guides, templates, alignment guides, a distractor and clamping instruments. The instrument for alignment of the cutting surface for resecting the tibia includes an ankle clamp, an adjustable alignment rod, and a cutting platform. After the cutting platform is properly aligned on the tibia, it is pinned thereto and the tibia may be resected using an oscillating saw. Also disclosed is a patella resection guide comprising a scissor-type clamp having distal gripping arms, each of which define a cutting surface, and gripping teeth.

Caspari, et al., U.S. Pat. Nos. 5,263,498, 5,228,459, and 5,304,181 disclose a method and apparatus for orthoscopically preparing bone surfaces for a knee replacement. A tibial jig is attached to the tibia at just above the ankle at a lower end and to just below the tibial tubercle at an upper end. One portal is formed in the knee for insertion of an orthoscope for viewing the knee, and another portal is formed for introducing resecting instruments. A cutting platform is aligned and secured in position and a cutting module is attached. Initially, a plunge cut across the tibial eminence is produced. This procedure is repeated until the surface of the tibial plateau is covered with trails having ridges therebetween. Thereafter, the device is passed back and forth over the tibial plateau to remove the ridges.

Morgan, U.S. Pat. No. 5,269,786, discloses a PCL oriented placement tibial guide method for guiding the tibial tunnel placement both inside and outside the knee in endoscopic ACL reconstruction.

Mikhail, U.S. Pat. No. 5,284,842, discloses a universal patellar clamp having an articular surface clamping member with a central aperture defining a centerline axis. An anterior clamping member is positioned along the centerline axis and is movable with respect to the articular clamping member to effect clamping of the patella for accepting a reamer for reaming a cavity in the patella of sufficient size to receive a patellar implant.

Johnson et al., U.S. Pat. No. 5,306,276, discloses a tibial resector guide including a tibial alignment jig having an ankle adjustment mechanism, a telescoping rod and a tibial resector guide which includes a head having a slot for receiving a bone saw. The head includes angled side walls along the slot which permit the guide to have a narrow anterior aperture, yet allow the saw blade to completely pass through the tibia.

Peterson, U.S. Pat. No. 5,342,368, discloses an intermedullary tibial resector guide which is affixed to the tibia by means of an intermedullary rod. An elongated bar extends from the intermedullary rod and carries a sleeve that supports a saw guide having a slot for receiving an oscillating saw.

Whitlock, et al., U.S. Pat. No. 5,147,365, discloses a patella osteotomy guide comprising a plier-like appliance with curved jaws for grasping a patella. A row of teeth face inwardly from the jaws and a rotating calibrated stylus measures the position of the patella with respect to an integral saw capture slot in each of the jaws. The jaws are curved with concave inner sides generally corresponding to the shape of a patella. With the guide attached to a patella, a sagittal saw can be passed through the saw capture slots to cut away a portion of the patella.

None of these previous efforts are as simple and easy to use as the present invention. Additionally, none of these previous efforts disclose all of the benefits and advantages of the present invention, nor do they teach or suggest all of the elements of the present invention.

OBJECTS AND SUMMARY OF THE INVENTION

It is a primary object of the present invention to provide a method and apparatus for properly resecting the proximal human tibia in connection with knee replacement surgery.

It is also an object of the present invention to provide a method and apparatus for resecting the proximal human tibia which minimizes the skill necessary to complete the procedure.

It is another object of the present invention to provide a method and apparatus for resecting the proximal human tibia which properly orients the resection of the proximal tibia.

It is even another object of the present invention to provide a method and apparatus for resecting the proximal human tibia which is easy to use.

It is yet another object of the present invention to provide a method and apparatus for resecting the proximal human tibia which orients the resection in accordance with what is desired in the art.

It is still yet another object of the present invention to provide a method and apparatus for resecting the proximal human tibia which minimizes the amount of bone cut.

It is a further object of the present invention to provide a method and apparatus for resecting the proximal human tibia which allows one to visually inspect the location of the cut prior to making the cut.

It is even a further object of the present invention to provide a method and apparatus for resecting the proximal human tibia which is simple in design and precise and accurate in operation.

It is yet a further object of the present invention to provide a method and apparatus for resecting the proximal human tibia which physically removes material from the proximal tibia along a surface dictated by a guide device.

It is still a further object of the present invention to provide a method and apparatus for resecting the proximal human tibia which employs a milling bit for removing material from the proximal tibia.

It is also object of the present invention to provide a method and apparatus for resecting the proximal human tibia which includes a component which is operated, and looks and functions, like pliers or clamps.

It is even another object of the present invention to provide an alternate embodiment of the method and apparatus for resecting the proximal human tibia which includes a component that resembles a U-shaped device for placing about the tibia.

It is even a further object of the present invention to provide an alternate embodiment of the method and apparatus for resecting the proximal human tibia which includes a component that resembles an adjustable, square, U-shaped device for placing about the tibia.

These objects and others are met and accomplished by the method and apparatus of the present invention for resecting the proximal tibia.

The apparatus of the present invention comprises a number of components including an ankle clamp, an alignment rod, a fixation head, cutting guide clamps having an integral attachment mechanism, and a milling bit.

The method of present invention includes the steps of attaching the ankle clamp about the ankle, interconnecting the distal end of the alignment rod with the ankle clamp, interconnecting the fixation head with the proximal end of the alignment rod, partially attaching the fixation head to the proximal tibia, aligning the alignment rod, completely attaching the fixation head to the proximal tibia, interconnecting the cutting guide clamps with the alignment rod, positioning the cutting guide clamps about the proximal tibia, securing the cutting guide clamps to the tibia at a proper location, removing the fixation head, and cutting the proximal tibia with the milling bit.

BRIEF DESCRIPTION OF THE DRAWINGS

Other important objects and features of the invention will be apparent from the following Detailed Description of the Invention taken in connection with the accompanying drawings in which.

1, wherein the cutting guide clamps interconnect with the alignment rod by means of a cutting guide clamp linkage.

Figure 1:
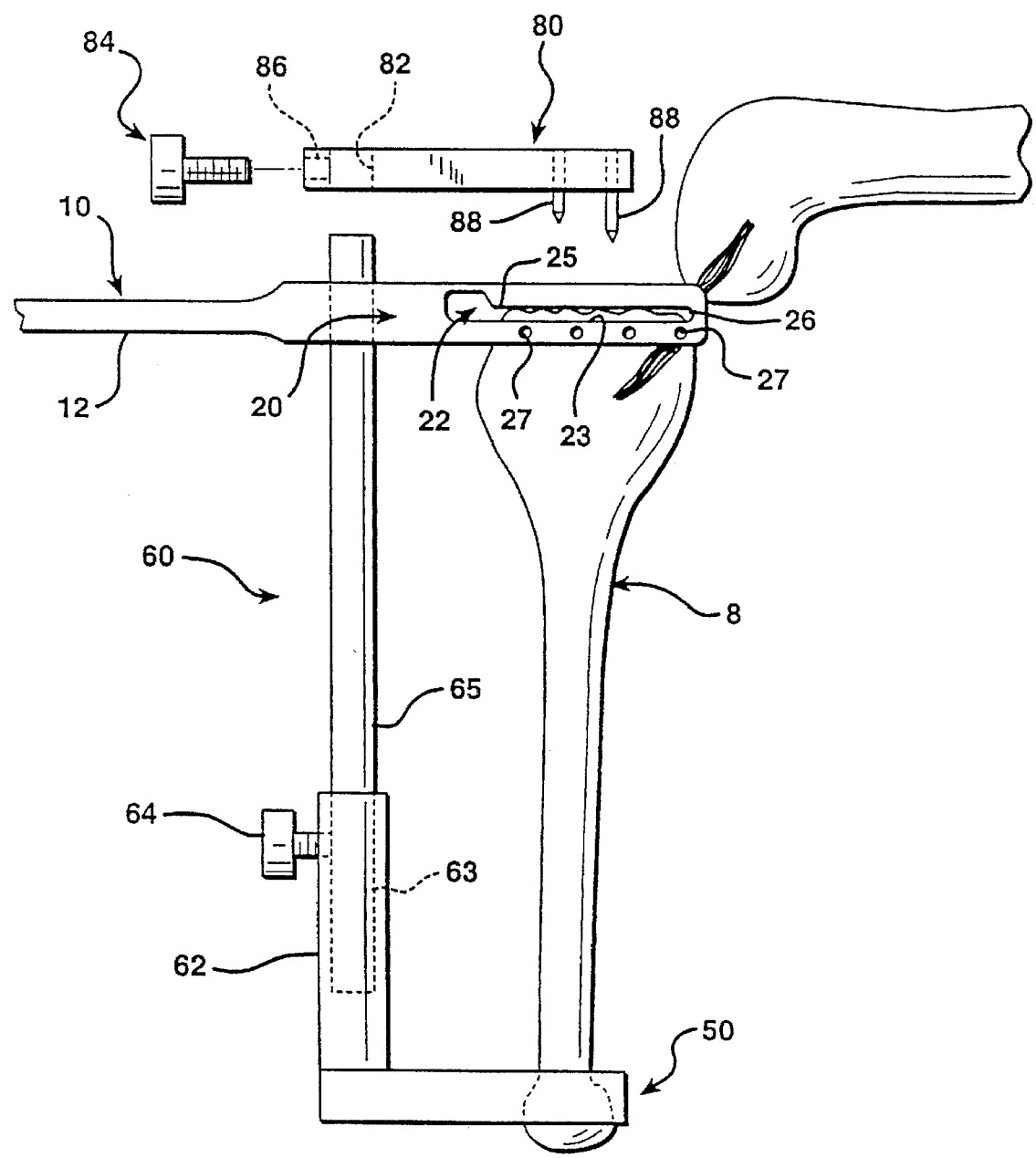
FIG. 1 is a partially exploded side plan view of an embodiment of the tibial resection apparatus of the present invention shown attached to the tibia, wherein the cutting guide clamps are of a fixed size and directly interconnect with the alignment rod.
Figure 4:
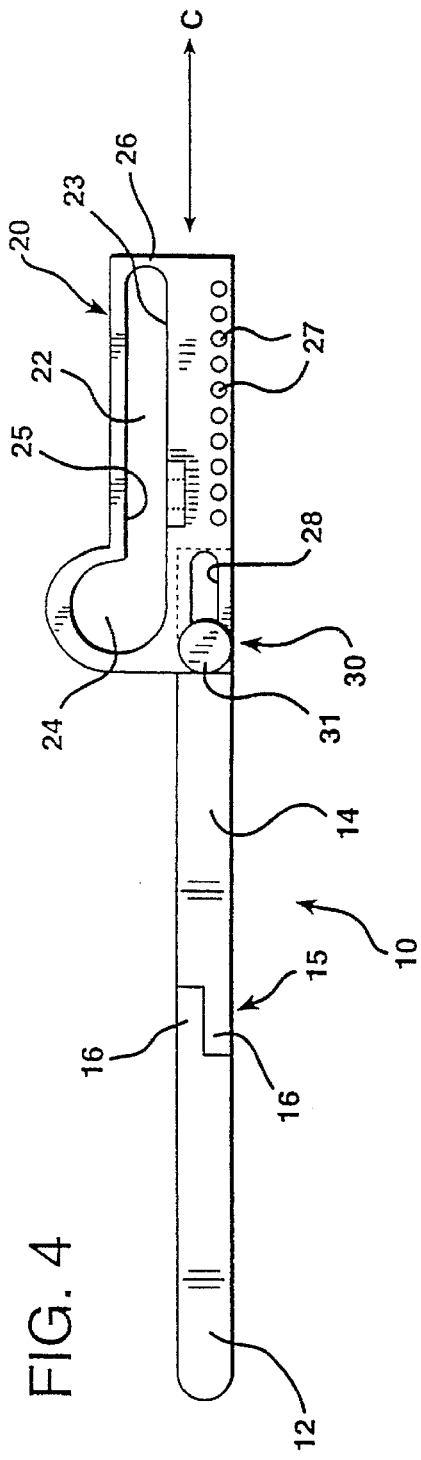

FIG. 4 is a side plan view of an embodiment of the cutting guide clamps shown in FIG. 1, wherein the cutting guide clamps are adjustable.

Figure 5:
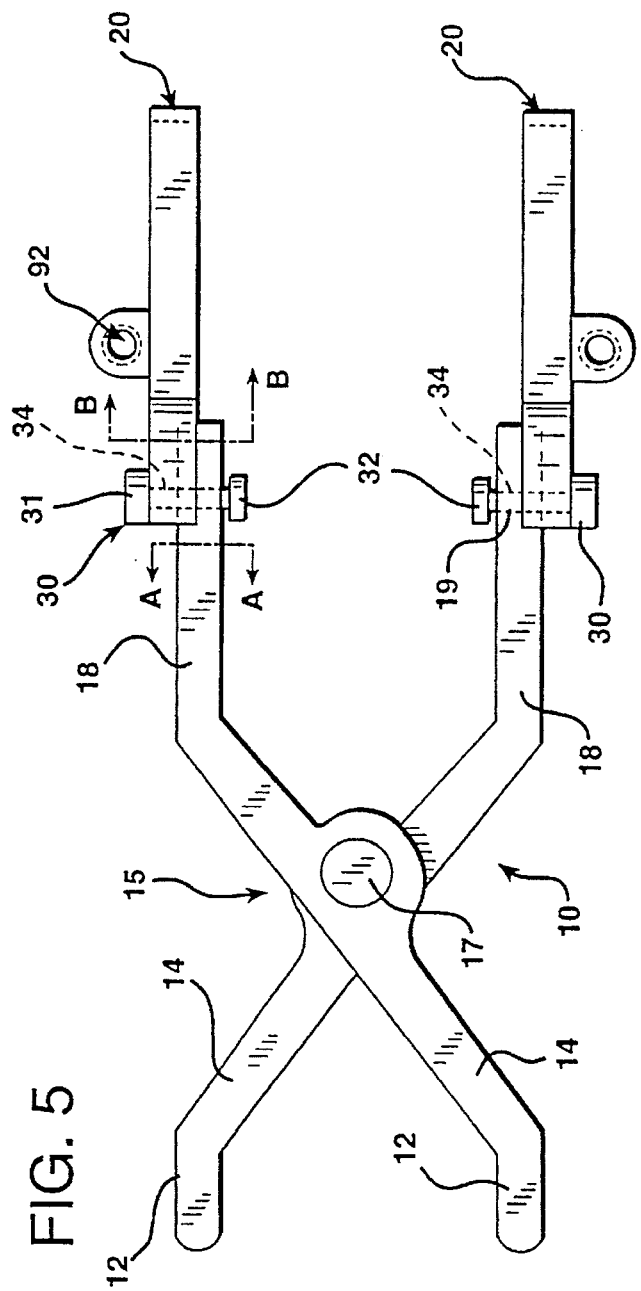

FIG. 5 is a top plan view of the cutting guide clamps shown in FIG. 4.

Figure 6:
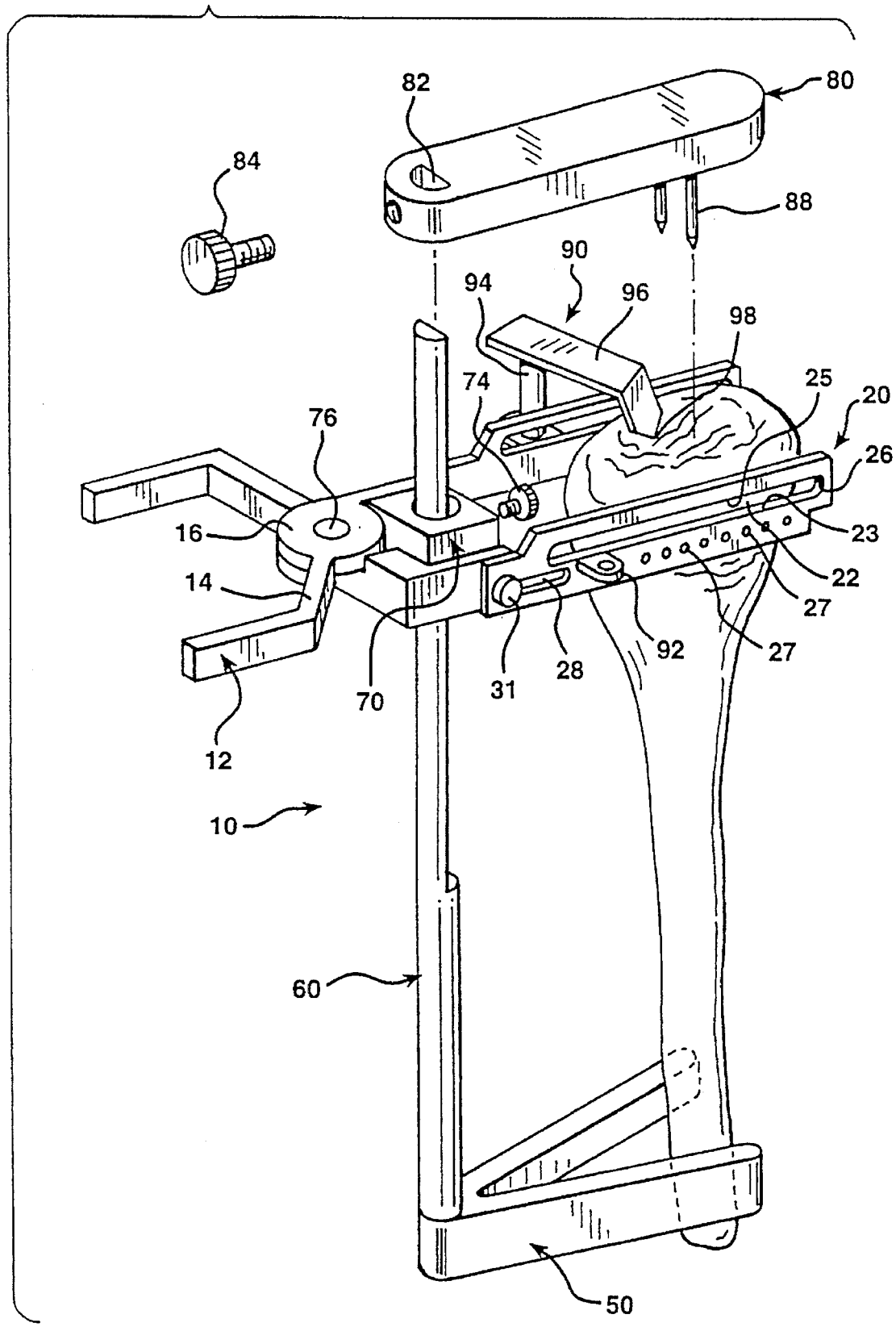

FIG. 6 is a perspective view of an embodiment of the tibial resection apparatus shown in FIG. 1, showing the proximal tibial referencing stylus attached to the cutting guide clamps.

Figure 7:
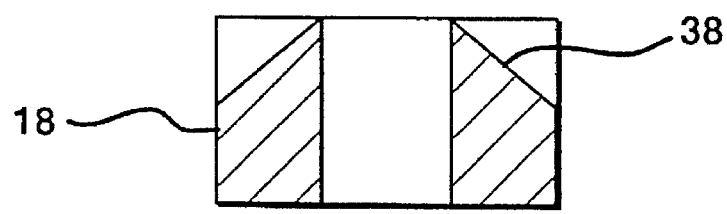

FIG. 7 is a cross-sectional view of the profile of the ends of the clamp members taken along line A—A in FIG. 5.

Figure 8:
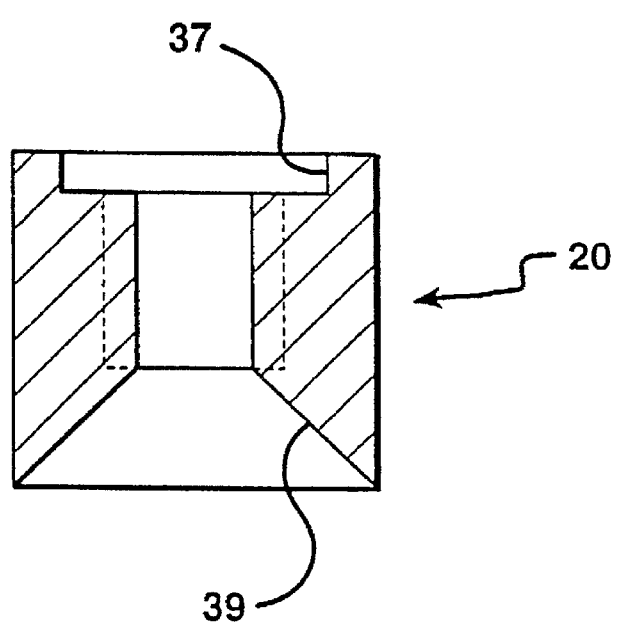

FIG. 8 is a cross-sectional view of the profile of the ends of the cutting guides taken along line B—B in FIG. 5, the ends of the clamps mating with the ends of the cutting guides for positioning the cutting guides with respect to the clamps.

Figure 9:
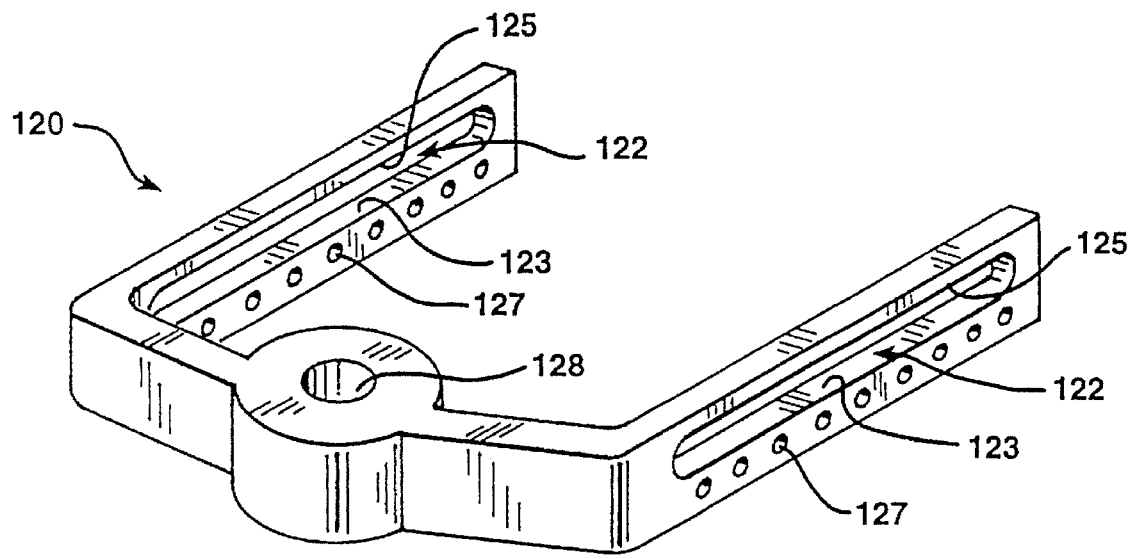

FIG. 9 is a perspective view of an alternate embodiment of a U-shaped cutting guide for use in the present invention.

FIG. 10 is a top plan view of another alternate embodiment of a square U-shaped cutting guide for use in the present invention.

Figure 11:
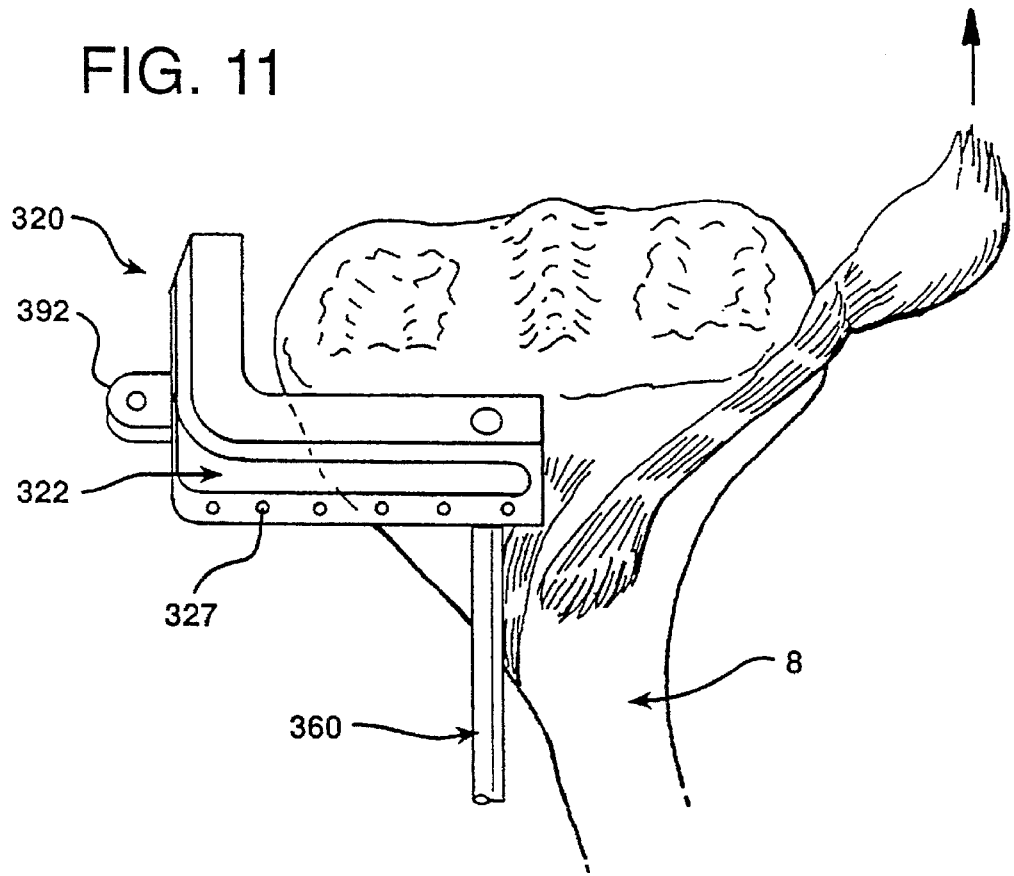

FIG. 11 is a perspective view of another alternate embodiment of a partial cutting guide for use in the present invention when the patellar tendon, patella, or quad tendon interferes with placement of the cutting guide about the tibia.

DETAILED DESCRIPTION OF THE INVENTION

Figure 2:
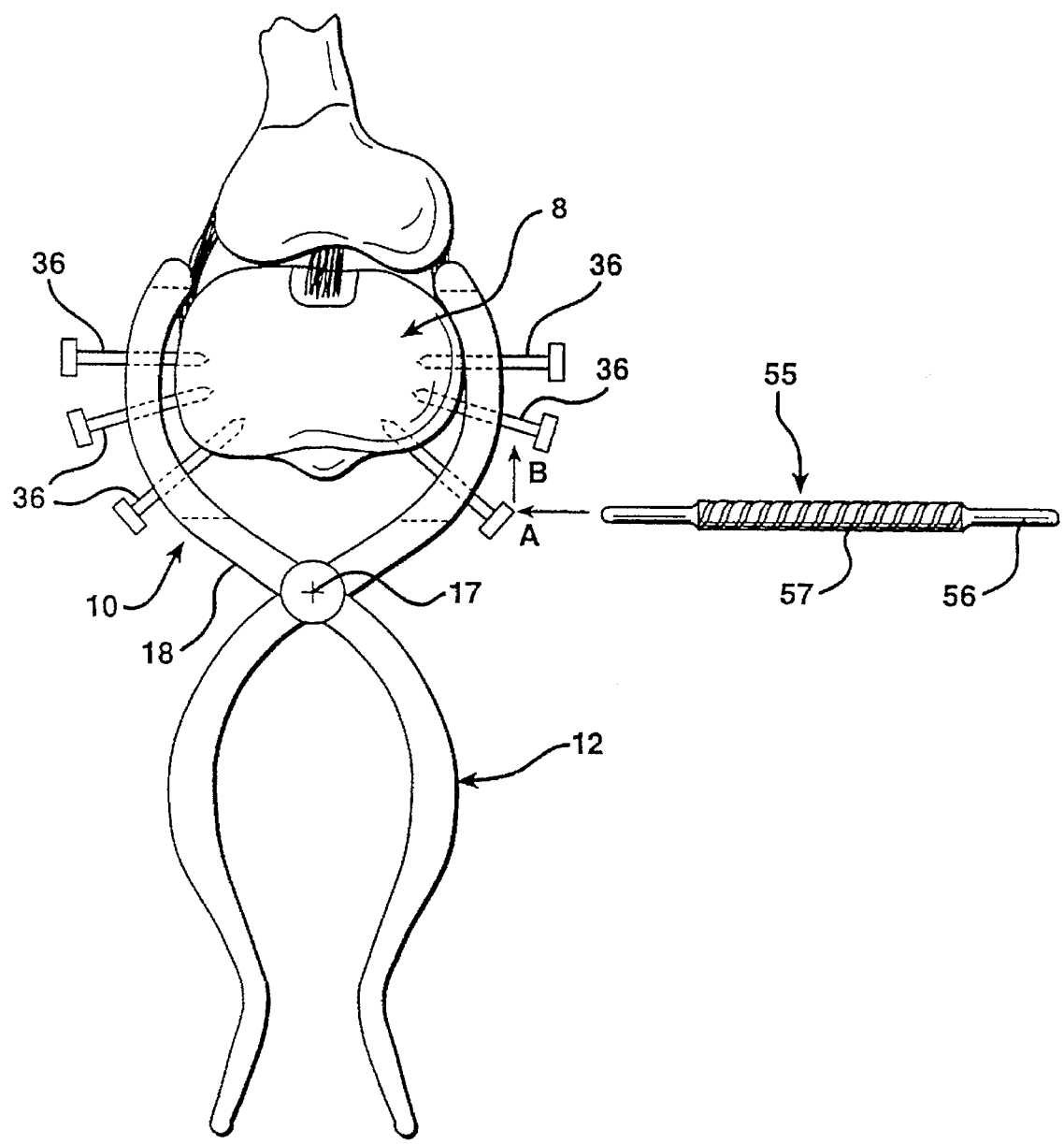
FIG. 2 is a top plan view of the tibial resection apparatus, shown in FIG. 1 prior to insertion of the milling bit into the apparatus.

As shown in FIGS. 1–6, the tibial resection apparatus of the present invention includes a number of components, namely, cutting guide clamps generally indicated at 10, cutting guides generally indicated at 20, ankle clamp generally indicated at 50, alignment rod generally indicated at 60, cutting guide clamp linkage generally indicated at 70, fixation block generally indicated at 80, proximal tibial referencing stylus generally indicated at 90, and milling bit generally indicated at 55. It should be noted that the cutting guides 20 may be formed integrally with the cutting guide clamps 10 as shown in FIGS. 1 and 2, or a separate members as shown in FIGS. 4, 5 and 6. Also, the cutting guides 20 may ride the alignment 60 as shown in FIGS. 1 and 2, or they may interconnect with the alignment rod 60 by means of cutting guide clamp linkage 70 as shown in FIGS. 4, 5 and 6.

As shown in FIG. 1, the ankle clamp 50 is attached at or just above the ankle and exterior to the skin. Any conventional ankle clamp may be used to firmly engage the ankle, or to engage the tibia above the ankle, to obtain a reference point for the other components of the present invention.

The ankle clamp is interconnected with and locked into place on the alignment rod 60 in any way known in the art. Preferably, though not necessarily, the alignment rod 60 is vertically adjustable with respect to the ankle clamp 50. This vertical adjustment can be achieved at the ankle clamp 50, at the interconnection of the ankle clamp 50 and the alignment rod 60, or within the alignment rod 60 itself. As shown in FIG. 1, the alignment rod includes a first lower end 62 having an aperture 63 extending vertically therein for telescopically receiving a second upper end 65 of the alignment rod 60. A set screw 64 is provided for fixing the upper end 65 with respect to the lower end 62.

The fixation block 80 is interconnected with an upper end of the alignment rod 60 by means of an aperture 82 in the fixation block 80 sized to receive the alignment rod 60 therethrough, or in any other manner known in the art. A set screw 84 may be provided to extend into the fixation block 80, through set screw aperture 86 in fixation block 80, to contact the alignment rod 60, to lock the fixation block 80 onto the alignment rod 60. The fixation block 80 additionally includes apertures extending vertically therethrough for receiving fixation pins 88 for affixing the fixation block 80 to the proximal tibia 8.

In operation, the ankle clamp 50 is attached about the ankle, or about the tibia just above the ankle, on the exterior of the skin. The fixation block 80 is already interconnected with the alignment rod 60. It is preliminarily positioned over the proximal tibia 8, and one of the fixation pins 88 is driven into the proximal tibia 8. Thereafter, the alignment rod 60 is adjusted to establish proper varus/valgus alignment and flexion/extension angulation as is conventionally known. Upon proper alignment of the alignment rod 60, the other fixation pin 88 is driven into the proximal tibia 8 to completely fix the fixation block 80 to the proximal tibia 8 to lock in the proper alignment of the alignment rod 60. Then, the fixation block 80 may be locked into position on the alignment rod 60.

Figure 3:
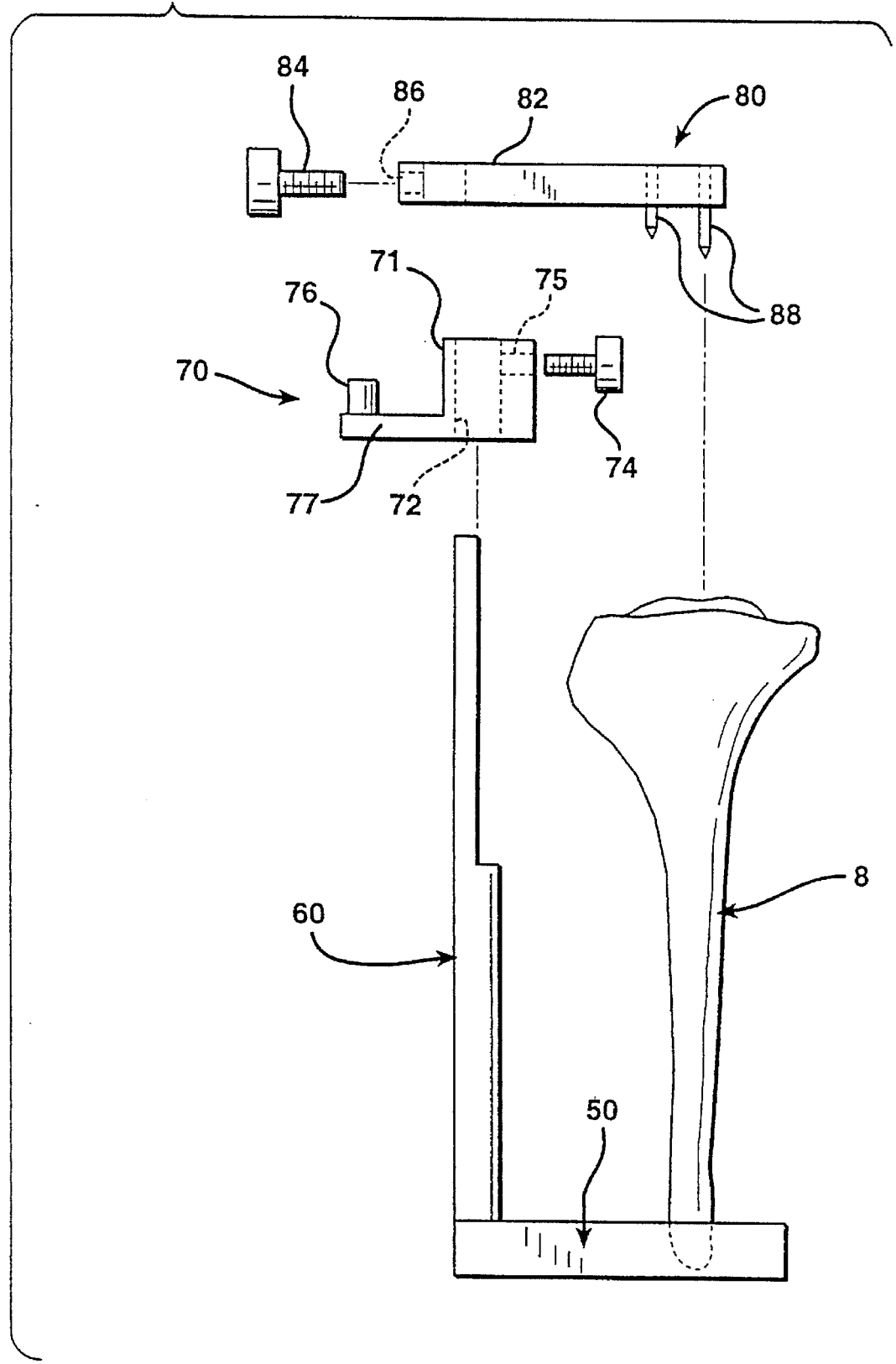
FIG. 3 is a partially exploded side plan view of another embodiment of the tibial resection apparatus shown in FIG.

After properly aligning and locking in the alignment of the alignment rod 60, the cutting guide clamps 10 and the cutting guides 20 may be employed. The cutting guide clamps 10 are interconnected with the alignment rod 60 by means of cutting guide linkage 70. Alternatively, the cutting guide clamps 10 could directly interconnect with the alignment rod 60 through apertures in the cutting guide clamps 10 as shown in FIGS. 1 and 2. As shown in FIG. 3, the cutting guide clamp linkage 70 comprises a body 71 having an alignment rod aperture 72 for receiving and riding the alignment rod 60 and a pivot locking set screw 74 which extends into the cutting guide clamp linkage 70 through set screw aperture 75 for contacting the alignment rod 60 and locking the cutting guide clamp linkage 70 with respect to the alignment rod 60. It should be pointed out that it may be desirable for the alignment rod 60 to have a flattened surface extending longitudinally along the alignment rod 60 for coacting with set screw 74 for maintaining proper alignment between the cutting guide clamp linkage 70 and the alignment rod 60.

The cutting guide clamp linkage 70 also includes a pivot shaft 76 rigidly interconnected with the body 71 of the cutting guide clamp linkage 70 by member 77 to position the pivot shaft 76 a distance away from the body 71 such that the cutting guide clamps 10 can be interconnected with the pivot shaft 76 and can be properly utilized without interfering with the body 71 of the cutting guide clamp linkage 70.

After the alignment rod 60 is properly aligned and locked into position, the cutting guide clamp linkage 70 is moved into its approximate desired position at the proximal tibia 8. It should be noted that the cutting guide clamp linkage 70 of present invention is positioned on the alignment rod 60 at the beginning of the procedure, prior to aligning the alignment rod 60, and prior to interconnecting the fixation block 80 with the alignment rod 60. However, it is within the scope of the present invention to provide a cutting guide clamp linkage 70 which is attachable to the alignment rod 60 after the alignment rod 60 has been aligned and locked into position.

After the cutting guide clamp linkage 70 is preliminarily approximately located, it is locked into place on the alignment rod 60. Thereafter, the cutting guide clamps 10 may be interconnected with the pivot shaft 76 by means of corresponding pivot apertures 17 in the cutting guide clamps 10.

As shown in FIGS. 4 and 5, the cutting guide clamps 10 include opposing hand grips 12 for grasping and manipulating the cutting guide clamps 10. Cross bar members 14 extend from the hand grips 12 to clamp members 18. The cross bar members 14 cross over each other at cross over point 15 whereat the cross bar members 14 have mating recessed portions 16 which function to maintain the hand grips 12 in the same plane as the clamp members 18. At the cross over point 15, the cross bar members 14 can pivot with respect to each other such that movement of the hand grips 12 towards each other moves the clamp members 18 together, and likewise, movement of the hand grip members 12 away from each other serves to move the clamp members 18 apart in the same manner as scissors or pliers. At the cross over point 15, the cross bar members 14 have corresponding pivot apertures 17 for receiving the pivot shaft 76 of the cutting guide clamp linkage 70. Thus, the cutting guide clamps 10 pivot about the pivot shaft 76 of the cutting guide clamp linkage 70. It should be noted that the cross bar members 14 could be interconnected with each other by a rivet or other means known in the art, or could be entirely independent pieces which coact as set forth above only upon being seated on pivot shaft 76.

The clamp members 18 of the cutting guide clamps 10 include cutting guide adjustment screw apertures 19 at the far ends thereof for receiving A-P adjustment screws 30 for adjustably interconnecting the cutting guides 20 with the clamp members 18, for adjustable movement in the direction shown by arrow C in FIG. 4. The clamp members 18 may be adjustably interconnected with the cutting guides 20 in any way known in the art. In one embodiment, the cutting guide adjustment screw apertures 18 are threaded and the cutting guides 20 have corresponding elongated apertures 28 extending over a portion of the length thereof for receiving the A-P adjustment screws at a desired location therealong. The A-P adjustment screws include a head 31, a retaining head 32, and a threaded shaft 34. When the cutting guides 20 are positioned correctly with respect to the clamp members 18, the A-P adjustment screws 30 are tightened down to lock the cutting guides 20 onto the clamp members 18 by actuating the head 31 to turn down the threaded shaft 34 with respect to the clamp member 18. Note the retaining head 32 of the A-P adjustment screws prevent the shaft 34 from being backed off out of engagement with the clamp member 18.

As shown in FIGS. 7 and 8, respectively, the clamp members 18 are shaped with opposing interior edges having chamfers 38 and the opposite exterior edges of the cutting guides 20 have mating recesses 39, both of said profiles extending along the contacting surfaces of the clamp members 18, as seen along line A—A in FIG. 5, and the cutting guides 20, as seen along line B—B in FIG. 5, to maintain a proper planar alignment therebetween. It should of course be noted that any other method known in the art may be employed to maintain the clamp members 18 and the cutting guides 20 in alignment. Additionally, the cutting guides 20 may include A-P adjustment screw recesses 37 for receiving the head 31 of the A-P adjustment screw 30.

The cutting guides 20 further include tibia attachment means for attaching the cutting guides 20 to the tibia 8. Any known attachment means may be employed to attach the cutting guides 20 to the tibia 8. As shown in FIGS. 2 and 4, a preferred attachment means for attaching the cutting guides 20 to the tibia 8 are pins 36 extending through pin apertures 27 in the cutting guides 20. The pins 36 may be captured in the pin apertures 27, or they may be entirely separate. Preferably, means exist on the cutting guides 20 for preliminarily attaching the cutting guides 20 to the tibia 8 prior to pinning the cutting guides 20 thereto, so that after proper positioning of the cutting guides 20, the hand grips 12 can be actuated by squeezing the hand grips 12 together to contact the cutting guides 20 against the tibia 8 so that the cutting guides 20 are preliminarily attached to the tibia 8. Such means may include a plurality of small pins captured by the cutting guide 20, or any other suitable means. After the preliminary attachment of the cutting guides 20 to the tibia 8, final attachment may be made by attachment pins 36 or by any other means known in the art.

The cutting guides 20, importantly, include cutting slots 22 which each comprise lower cutting slot guide surface 23 and upper cutting slot retaining surface 25, as well as cutting slot entrance and exit 24 at one end thereof and cutting slot end wall 26 at the other end thereof. The cutting slot 22 is of a length sufficient to extend across the proximal tibia 8, at a desired angle to the intermedullary canal, at the widest point of the proximal tibia 8, to allow the entire upper surface of the proximal tibia 8 to be cut. The cutting slot 22 is of a size sufficient to receive a cylindrical milling bit 55 such as that shown in FIG. 2 and described in co-pending patent application No. 08/300,379, filed Sep. 2, 1994 by Goldstein, et al. The milling bit 55 comprises central cutting portion 57 having helical cutting teeth along its length for cutting bone. The milling bit 55 further comprises spindles 56 extending from the central cutting portion 57 for supporting the central cutting portion 57.

The milling bit 55 is inserted into and received in the cutting slot 22 through cutting slot entrance 24, along the direction shown by arrow A in FIG. 2. Note that the cutting slot entrance 24 may by of a wider slot area or an upturned portion of the slot 22 or the milling bit 55 may merely be inserted and removed from the slot 22 at an end thereof. The spindles 56 extend through and coact with the lower cutting guide surface 23 and the upper retaining surface 25 of the cutting slot 22 to guide the milling bit 55 along the cutting slot 22 to resect the proximal tibia 8, along the direction shown by arrow B in FIG. 2. At an end of one or both of the spindles 56 is a means for engaging the milling bit 55 with a drive means such as an electric drill, or other drive means. This engagement means may include a hexagonal head on one of the spindles, or any other suitable method of engagement known in the art. Additionally, bushings may be employed, either on the milling bit 55 or captured by the cutting slot 22, to provide a non-metallic bearing between the spindles 56 of the milling bit 55 and the cutting slot 22 to avoid galling and to insure smooth articulation of the milling bit 55 along the cutting slots 22. Importantly, the configuration of the milling bit 55 may be varied in accordance with what is known in the art, as long as the cutting device can follow the cutting path of the cutting slot to resect the proximal tibia. Additionally, it should also be pointed out that other cutting tools may be used in accordance with present invention, including an oscillating or reciprocating saw or other means for resecting the tibia by following the cutting slots on the cutting guides.

After the cutting guide clamps 10 are preliminarily located along the alignment rod 60, the cutting guides 20 are adjusted with respect to the clamp members 18 for proper anterior-posterior positioning to extend along the proximal tibia 8 for guiding the milling bit 55. Importantly, the cutting slots 22 should extend beyond the edges of the proximal tibia 8. Once proper anterior-posterior alignment is obtained, the cutting guides 20 may be locked into place on the clamp members 18.

Thereafter, a proximal tibial referencing stylus 90 may be attached to a referencing bracket 92 on the cutting guides 20.

The referencing bracket 92 may be positioned in any location on the cutting guides 20, or on any other convenient component of the tibia resection system of the present invention. Alternatively, the referencing stylus 90 may be formed as part of a component of the present invention, or as a separate component which could function merely by contacting the cutting guides 20 of the present invention of any other component thereof. The referencing stylus 90 shown in FIG. 6 includes stylus body 94 which may be interconnected with the referencing bracket 92 in any manner known in the art, preferably by a quick release and connect mechanism or a threaded connection. The stylus body 94 supports a stylus arm 96, which is rotatable with respect to the stylus body 94 and configured to extend out and down from the stylus body 94 to contact the proximal tibia 8 at a tip 98 of the stylus arm 96. The stylus body 94, arm 96 and tip 98 are sized to contact the proximal tibia 8 to reference the positioning of the cutting guides 20 to cut the proximal tibia at a proper distance below the proximal tibia 8 as is known in the art. The stylus arm 96 may include more than one tip 98, such other tips extending down from the stylus body 94 in varying distances.

In operation, one determines the desired location of the stylus tip 98, unlocks the cutting guide clamp linkage 70 to permit the linkage 70 to move up and down the alignment rod 60, and places the tip 98 on the lowest point of the proximal tibia 8 to reference the position of the of the cutting guides with respect to the proximal tibia 8 and with respect to the alignment rod 60. Thereafter, the cutting guide clamp linkage 70 is locked to the alignment rod 60 to lock the cutting guides 20 into the proper position on the alignment rod 60, and accordingly, into proper position with respect to the proximal tibia 8. Thereafter, the hand grips 12 are actuated to press the cutting guides 20 against the proximal tibia 8 to preliminarily lock them into position on the proximal tibia 8. Next, the cutting guides 20 are fixed to the proximal tibia 8 by pins 36 or any other desired fixation means. The fixation block 80 can then be removed from the proximal tibia 8, and the proximal tibia 8 may be resected.

The cutting operation is similar to the cutting operation set forth in co-pending patent application No. 08/300,379, filed Sep. 2, 1994 by Goldstein, et al. Essentially, the cutting operation comprises inserting the milling bit 55 into the cutting guide slots 22 through the slot entrance/exit 24 to position the central cutting portion 57 between the cutting guides 20, the spindles 56 extending through the cutting guide slots 22. After the milling bit 55 is positioned, the drive means may be interconnected therewith, actuated, and the milling bit 55 moved along the cutting slots 22 to resect the proximal tibia 8.

It should be noted that a handle may be provided for attachment to the spindle which is not driven so that such spindle may be guided evenly through the cutting slots 22 to facilitate the cutting procedure. Alternatively, a handle can be provided which interconnects with both spindles to further facilitate control of the milling bit 55 during the cutting procedure. Additionally, the bushings that fit over the spindles 56 of milling bit 55 and ride in the cutting slots 22 may be captured in the ends of the handle and the milling bit received therethrough.

Additionally, it should be pointed out that it is within the scope of the present invention to modify the cutting slots 22 such that the upper retaining surface is eliminated, and the milling bit 55 merely follows the lower cutting guide surface 23. With the cylindrical milling bit 55 herein described, this is especially viable as the milling bit 55 tends to pull down into the bone as it is cutting, thereby primarily utilizing the lower cutting guide surface 23 of the cutting guide 20.

As shown in FIGS. 9–11, various other embodiments of the cutting guides are considered within the scope of the present invention. The cutting guide 120 shown in FIG. 9 is of a generally U-shaped configuration, having cutting guide slots 122, lower cutting guide surface 123, upper retaining surface 125, pin apertures 127 and alignment rod aperture 128. This cutting guide 120 is used in the same manner as the cutting guides hereinbefore described, the differences being that the cutting guide 120 interconnects directly with the alignment rod and that various size cutting guides must be provided to accommodate various sized tibias.

Likewise, the cutting guide 220 shown in FIG. 10 operates in the same manner as the cutting guide devices hereinbefore described, but it does not include cutting guide clamps. The cutting guide 220 includes cutting slots 222, and it interconnects directly with alignment rod by means of aperture 228. The distance between facing members 230 can be adjusted by moving base members 232 and 234 with respect to each other to size the cutting guide 220 for the tibia to be cut. Upon proper sizing, the base members 232 and 234 may be locked with respect to each other by set screw 236 or any other means known in the art.

FIG. 11 shows an embodiment of the cutting guide for use when the patellar tendon, the patella, or the quad tendon interferes with the placement of the other cutting guides of the present invention. As shown in FIG. 11, the cutting guide 320 may be directly interconnected with the alignment rod, and positioned on the tibia as hereinbefore set forth. Basically, this embodiment of the invention includes only one cutting guide. The cutting guide 320 and the cutting guide slot 322 may be wider than in the previous embodiments to help stabilize the milling bit in operation. In this embodiment, the milling bit may be first plunged across the tibia, and then moved therealong. The milling bit may be spring loaded to increase resistance as it is plunged through the cutting guide to bias the bit against being plunged too far across the tibia to cause damage to the tissue about the tibia. Additionally, a support member, not shown, could be provided to extend from the cutting guide 320, over and across the tibia to the other side thereof where it could have a slot to capture the milling bit and provide additional support thereto.

Having thus described the invention in detail, it is to be understood that the foregoing description is not intended to limit the spirit and scope thereof. What is desired to be protected by Letters Patent is set forth in the appended claims.

What is claimed is:

1. A method for resecting a proximal tibia comprising the steps of:
   attaching an ankle clamp about an ankle;
   interconnecting an alignment rod at a distal end thereof with the ankle clamp;
   interconnecting a fixation head with a proximal end of the alignment rod;
   partially attaching the fixation head to the proximal tibia;
   aligning the alignment rod;
   completely attaching the fixation head to the proximal tibia;
   interconnecting cutting guide clamps with the alignment rod;
   positioning the cutting guide clamps about the proximal tibia;
   securing the cutting guide clamps to the tibia at a proper location;
   removing the fixation head from the tibia; and
   cutting the proximal tibia with a milling bit.

2. The method of claim 1 wherein the step of interconnecting the cutting guide clamps with the alignment rod further includes the steps of:

positioning a cutting guide linkage along the alignment rod; and interconnecting the cutting guide clamps with the cutting guide linkage by means of locating pivot apertures in the cutting guide clamps onto a pivot shaft formed on the cutting guide linkage.

3. The method of claim 2 wherein the step of positioning the cutting guide clamps about the proximal tibia comprises manipulating hand grips interconnected with the cutting guide clamps to move the cutting guide clamps against the proximal tibia.

4. The method of claim 3 wherein the step of positioning the cutting guide clamps about the proximal tibia further includes the step of adjusting the cutting guide clamps with respect to cutting guide members extending from the hand grips.

5. The method of claim 4 wherein the step of cutting the proximal tibia with a milling bit comprises the steps of:

inserting the milling bit into guide slots formed in the cutting guide clamps;

engaging the milling bit with drive means;

capturing ends of the milling bit with handle means; and guiding the milling bit through the guide slots in the cutting guide clamps to resect the proximal tibia.

6. An apparatus for resecting a proximal human tibia comprising:

alignment means having proximal and distal ends;

distal attachment means for attaching to a tibia, the distal attachment means interconnected with the distal end of the alignment means;

fixation means for attachment to the proximal tibia, the fixation means interconnected with the proximal end of the alignment means for aligning the alignment means;

cutting guide means interconnected with the alignment means, the cutting guide means comprising two members in opposing relationship including:

guide surfaces defining linear paths located within cutting guide slots formed in the cutting guide means;

entrance areas comprising upturned slot areas communicating with the cutting guide slots for receiving a milling bit;

the cutting guide means including hand grips, mating cross bars having pivot apertures and clamp members, the cutting guide means adjustably interconnected with the clamp members;

fixation means for affixing the cutting guide means to a tibia; and milling means for cutting a tibia, the milling means received and guided by the cutting guide slot of the cutting guide means for resecting a tibia.

7. The apparatus of claim 6 further including cutting guide linkage means for interconnecting the cutting guide means with the alignment means, the cutting guide linkage means comprising an aperture for receiving the alignment rod and a post for inserting through the pivot apertures of the mating cross bars of the cutting guide means.

8. An apparatus for resecting a proximal human tibia comprising:

alignment means having proximal and distal ends;

distal attachment means for attaching to the tibia, the distal attachment means interconnected with the distal end of the alignment means;

fixation means for attachment to the proximal tibia, the fixation means interconnected with the proximal end of the alignment means for aligning the alignment means;

cutting guide means interconnected with the alignment means, the cutting guide means comprising cutting guides positionable in opposing relation along sides of the tibia, the cutting guides including cutting guide surfaces and fixation means for affixing the opposing cutting guides to opposing sides of the tibia; and milling means for cutting the tibia, the milling means coacting with the cutting guide surfaces of the cutting guide means for resecting the tibia.

9. The apparatus of claim 8 wherein the guide surfaces of the cutting guides are located within cutting guide slots formed in the cutting guides, the cutting guide slots receiving and guiding the milling means for resecting the tibia.

10. The apparatus of claim 9 wherein the guide surfaces of the cutting guide slots define a linear cutting path.

11. The apparatus of claim 8 wherein cutting guides have corresponding cutting guide slots therein for receiving and guiding the milling means for resecting the tibia.

12. The apparatus of claim 11 wherein the cutting guide slots further include an entrance area for receiving the milling means comprising an enlarged slot area at an end of the guide slots.

13. The apparatus of claim 11 wherein the cutting guide slots further include an entrance area for receiving the milling means comprising an upturned slot area at an end of the guide slots.

14. The apparatus of claim 11 wherein the cutting guide means further comprise hand grips, mating cross bars having pivot apertures and clamp members, the cutting guide means adjustably interconnected with the clamp members.

15. The apparatus of claim 14 further including cutting guide linkage means for interconnecting the cutting guide means with the alignment means, the cutting guide linkage means comprising an aperture for receiving the alignment rod and a post for inserting through the pivot apertures of the mating cross bars of the cutting guide means.

16. A method for resecting a proximal tibia comprising the steps of:

interconnecting an alignment rod with the tibia at proximal and distal ends of the tibia;

interconnecting cutting guide means with the alignment rod;

positioning the cutting guide means in opposing relation along sides of the proximal tibia;

securing the cutting guide means to opposing sides of the tibia;

cutting the proximal tibia with a milling bit by moving the milling bit along cutting guide surfaces on the cutting guide means.

17. The method of claim 16 wherein the step of positioning the cutting guide means in opposing relation across the proximal tibia comprises manipulating hand grips interconnected with the cutting guide means to move the cutting guide means against the proximal tibia.

18. The method of claim 17 wherein the step of positioning the cutting guide means in opposing relation across the proximal tibia further includes the step of adjusting the cutting guide means with respect to the hand grips.

19. The method of claim 18 wherein the step of cutting the proximal tibia with a milling bit comprises the steps of:

inserting the milling bit into guide slots formed in the cutting guide means;

engaging the milling bit with drive means;

capturing ends of the milling bit with handle means; and guiding the milling bit through the guide slots in the cutting guide means to resect the proximal tibia.

* * * * *